United States Patent [19]
Kirk et al.

[11] Patent Number: 4,951,680
[45] Date of Patent: Aug. 28, 1990

[54] FETAL MONITORING DURING LABOR

[75] Inventors: Derrick L. Kirk, Nottingham; Henry Murray, Giltbrook, both of England

[73] Assignee: National Research Development Corporation, London, England

[21] Appl. No.: 250,254

[22] Filed: Sep. 27, 1988

[30] Foreign Application Priority Data

Sep. 30, 1987 [GB] United Kingdom ................ 8722899

[51] Int. Cl.$^5$ ............................................. A61B 5/04
[52] U.S. Cl. .................................... 128/698; 128/696; 128/702; 128/708
[58] Field of Search ............... 128/698, 696, 702, 703, 128/704, 708

[56] References Cited

U.S. PATENT DOCUMENTS

| | | | |
|---|---|---|---|
| 3,822,696 | 7/1974 | Ekstrom et al. | 128/703 |
| 4,211,237 | 7/1980 | Nagel | 128/696 |
| 4,537,200 | 8/1985 | Widrow | 128/696 |
| 4,569,356 | 2/1986 | Kyozuka | 128/698 |

FOREIGN PATENT DOCUMENTS

2902097  7/1980  Fed. Rep. of Germany .

OTHER PUBLICATIONS

K. H. Lee, "Observations on the Configuration of the Fetal Electrocardiogram Before and During Labour", The Journal of Obstetrics and Gynaecology of the British Commonwealth, Jan. 1974, vol. 81, pp. 61–69.
Murray, "The Fetal Electrocardiogram; Current Clinical Developments in Nottingham", J. Perinat. Med. 14, (1986), pp. 399–404.
V. M. Roemer, M.D. et al., Direct Foetal Electrocardiography in Management of High Risk Pregnancies (From the Department of Obstetrics and Gynaecology of the University Basel), pp. 135–138.
E. M. Southern, M.D., "Fetal Anoxia and its Possible Relation to Changes in the Prenatal Fetal Electrocardiogram", American Journal of Obstetrics and Gynecology, vol. 73, Feb. 1957, No. 2, pp. 233–247.
G. Pardi et al., "Fetal Electrocardiogram Changes in Relation to Fetal Heart Rate Patterns During Labor", Am. J. Obstet. Gynecol., Jan. 15, 1974, pp. 243–250.
C. J. Marvell et al., "The Normal Condition of the Fetal Electrocardiogram During Labour", Am. J. Obstet. Gynecol., Sep. 1980, vol. 87, pp. 786–796.
D. MacDonald et al., "The Dublin Randomized Controlled Trial of Intrapartum Fetal Heart Rate Monitoring", Am. J. Obstet., Jul. 1, 1985, vol. 152, No. 5, pp. 524–539.
J. E. A. Sheild et al., "The Use of Digital Filters in Enhancing the Fetal Electrocardiogram", J. Biomed. Engng., 1981, vol. 3, Jan., pp. 44–48.
D. L. Kirk et al., "Techniques for the Routine On-Line Processing of the Fetal Electrocardiogram", J. Perinat. Med. 14, (1986), pp. 391–398.
C. J. Marvell et al., "A Simple Software Routine for the Reproducible Processing of the Electrocardiogram", J. Biomed. Engng., 1980, vol. 2, Jul., pp. 216–220.
H. M. L. Jenkins et al., "Can Fetal Electrocardiography Improve the Prediction of Intrapartum Fetal Aciodsis?", British Journal of Obstetrics and Gynaecology, Jan. 1986, vol. 93, pp. 6–12.

*Primary Examiner*—Francis Jaworski
*Assistant Examiner*—George Manuel
*Attorney, Agent, or Firm*—Cushman, Darby & Cushman

[57] ABSTRACT

Apparatus for monitoring fetal health during labor detects the occurrence of a fetal ECG in digital signals derived from electrodes on a fetus using a matched filter routine to detect a QRS complex. The peaks of successive R waves are then found and used to determine fetal heart rate. After time coherent filtering of digital samples representing the fetal ECG the P-R interval and the elevation of the S-T interval are found and a correlation coefficient between the fetal heart rate and the P-R interval is derived. The elevation and the coefficient are displayed. If the correlation coefficient becomes positive for about half an hour and a significant fall in the elevation of the S-T interval also occurs it is an indication of acidosis of the fetus.

24 Claims, 9 Drawing Sheets

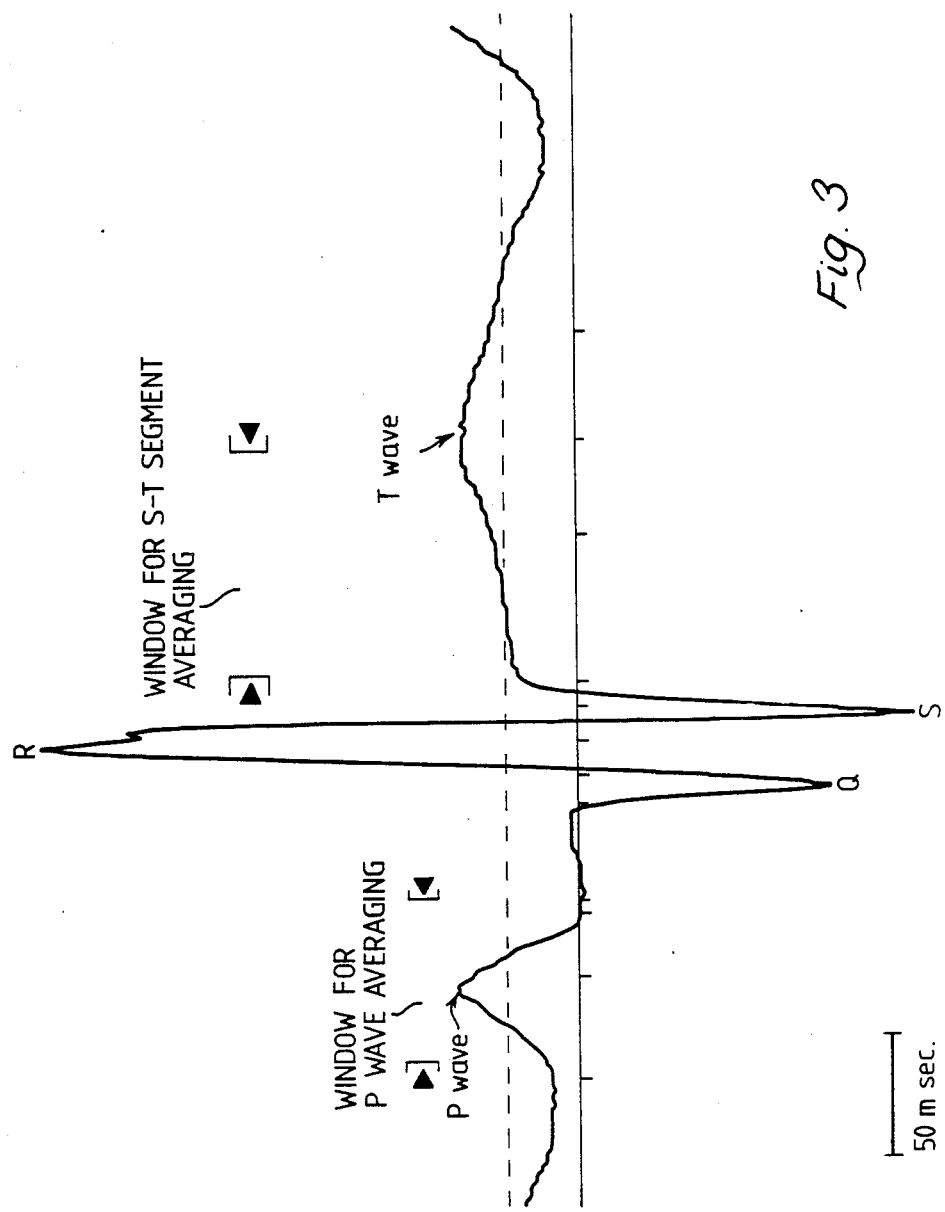

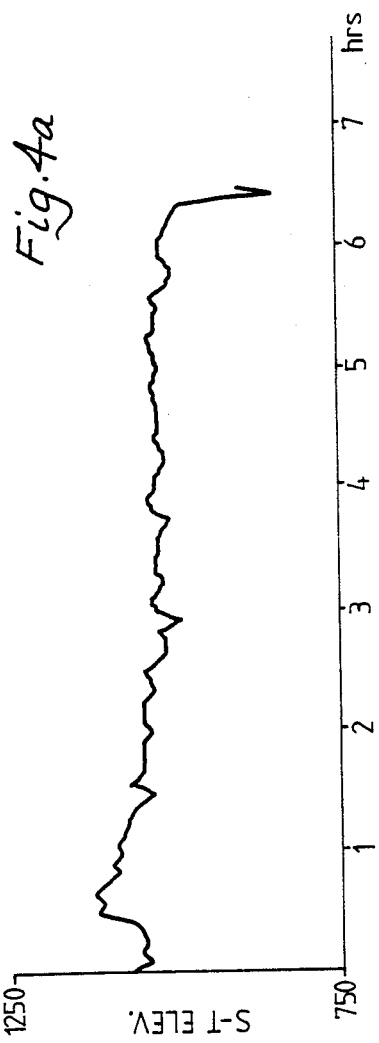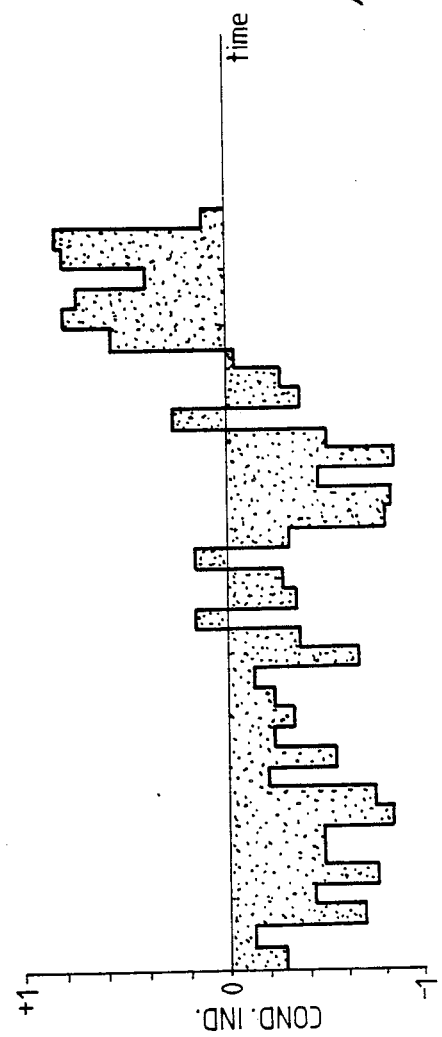

FETAL MONITORING DURING LABOR

FIELD OF THE INVENTION

The present invention relates to monitoring fetal health during labor.

BACKGROUND OF THE INVENTION

The present inventors have become aware that changes in that part of the fetal electrocardiogram (FECG) known as the P-R interval (that is the time interval between the peak and the P wave and the R peak—see FIG. 3) herald a deterioration in the acid-base status of fetal blood. Previous reports of P-R interval changes have been both infrequent and, in part, contradictory. In papers, dated 1974 and before, and probably based on the analysis of recorded measurements taken during labor, one reported direct correlation between the duration of P-R interval and fetal heart rate (FHR) (although not when there was fetal tachycardia) and another that the P-R interval shortened with decelerating FHR. In another such paper a shortening of the P-R interval with acidosis was noted, while a different paper reported a long-term trend for the P-R interval to diminish towards the end of labor. A shortening or lengthening of the P-R interval with decelerations in FHR late in labor was also separately reported.

SUMMARY OF THE INVENTION

According to a first aspect of the present invention there is provided a method of monitoring fetal health during labour comprising the steps of repeatedly deriving a signal representative of the P-R interval of the fetal heart, repeatedly deriving a signal representative of the period of the fetal heart, and repeatedly deriving a signal representative of the relationship between the directions of change, firstly, of the P-R interval and, secondly, the fetal heart rate or the repetition period of the operation of the fetal heart to provide an indication of fetal health.

According to a second aspect of the invention there is provided apparatus for monitoring fetal health during labor comprising means for repeatedly deriving a signal representative of the P-R interval of the fetal heart, for repeatedly deriving a signal representative of the period of the fetal heart, and for providing an indication of the relationship between directions of change, firstly, of the P-R interval and, secondly, the fetal heart rate or the repetition period of the operation of the fetal heart to provide an indication of fetal health.

In providing the said indication, the FHR is usually used as the signal representative of the period of the fetal heart.

The said means usually includes a programmed special purpose computer comprising at least one integrated circuit processor, and in both the method and apparatus of the invention the said signals are usually digital signals existing in an operating computer.

Preferably the method of the invention includes deriving an indication of the correlation between the duration of the P-R interval and the FHR or the repetition period of the FECG to provide an indication of the said relationship. Apparatus according to the invention preferably includes means for deriving the said correlation.

The present inventors have found that in a healthy fetus the correlation between the duration of the P-R interval and the FHR is negative but when acidosis, indicating hypoxia, occurs this correlation becomes positive. Thus the inventors have found that the P-R interval may lengthen or shorten with fall in FHR and while the former r is an indication of a healthy fetus, the latter indicates probable hypoxia.

However, comparatively short periods, for example 10 minutes, of positive correlation between the duration of the P-R interval and the FHR can occur even in a healthy fetus and for this reason a comparatively long period, for example half an hour, of positive correlation should occur before it is considered that acidosis has occurred. Even then it is believed to be sensible to wait for a significant fall in the elevation of the S-T interval of the FECG before confirming acidosis.

Thus the method of the present invention preferably includes repeatedly measuring the elevation of the S-T interval and similarly the apparatus of the invention preferably also includes means for repeatedly measuring the S-T elevation.

An important advantage of the invention therefore is that a reliable indication of fetal hypoxia is given, it is believed by the value of the correlation between the FHR and P-R interval when these quantities are measured repeatedly and the correlation is derived on-line. This is particularly true when an on-line indication of the elevation of the S-T interval is also given.

The present inventors believe that the following physiological explanation explains why the method and apparatus of the invention can be used in detecting acidosis. Under normal oxygen supply there is a negative correlation between the P-R interval and heart rate as has been observed in the exercising adult human. Exercise causes adrenalin to rise causing an increase in heart rate and a decrease in the P-R interval. At the beginning of labor respiration is aerobic and a "normal" negative correlation between the FHR and the P-R interval occurs. In the second stage of labour oxygen levels in the blood supplied to the fetus are likely to fall and this causes, as is normal in such circumstances, adrenalin production. As a result the FHR rises and the P-R interval falls. However, if the oxygen supply continues to fall so that hypoxia sets in then the fetus switches to anaerobic respiration with the result that the lactic acid is produced and acidosis begins to occur. The low oxygen supply causes the fetal heart rate to drop which as expected causes adrenalin to be produced by the fetus so that the P-R interval is shortened. However the fetal heart rate is not greatly increased by the high adrenalin level and the expected increase in FHR appears to be overridden by the low oxygen supply. Thus the inverse relationship between FHR and P-R interval is reversed and the fetal heart rate correlates positively with the P-R interval. Results of recorded measurements made from fetal lambs under conditions of partial and complete acute hypoxia suggest that the alteration in the correlation between the FHR and the P-R occurs at a time of lactic acid production.

The coefficient of correlation between the FHR and the P-R interval is known by the inventors as the Conduction Index and from the above discussion the Conduction Index appears to identify those fetuses in which some degree of anaerobic respiration is occurring and, therefore, those fetuses at risk from hypoxia during labor.

Preferably the method (and apparatus) of the invention also includes finding (or means for finding) the conduction index by deriving the Pearson coefficient of correlation as the index. An expression for this coefficient is given later.

As stated, the Pearson coefficient requires the calculation of the correlation coefficient between the P-R interval and the FHR. This can be done instantaneously in real time. Typically, these two quantities are averaged over intervals of about one minute (one minute plus or minus 20 percent), and some ten pairs (ten plus or minus two) are used to calculate the Pearson coefficient. This procedure acts as a form of filtering that eliminates spurious responses while retaining sufficient clinical sensitivity. The intervals of time, and number of pairs, can be varied in order to change the sensitivity of the conduction index in responding to changes in fetal distress.

A further advantage of the invention is that if the conduction index is calculated in this way then the quantities required can be obtained without very complicated processing so allowing a reasonable economical monitoring apparatus to be manufactured. Also the conduction index allows a display to be generated which indicates trends without too many variations due to temporary disturbances. Apparatus according to the invention may conveniently display conduction index, S-T elevation, fetal heart rate and inter-uterine pressure (IUP). Although the latter two quantities are being questioned recently as indicators of fetal health, it is believed that they should be displayed to provide continuity with previous instrumentation.

BRIEF DESCRIPTION OF THE DRAWINGS

Certain embodiments of the invention will now be described by way of example, with reference to the accompanying drawings, in which:

FIG. 3 is an example of an enhanced FECG, FIG. 4 shows a reconstruction of conduction index and S-T elevation which occurred during a birth and is given as an example of the type of display which may be given by the apparatus of FIG. 1, FIGS. 5a and 5b show a flow chart of a preferred alternative L algorithm for determining the conduction index and S-T elevation.

DETAILED DESCRIPTION OF THE INVENTION

Figure 1:
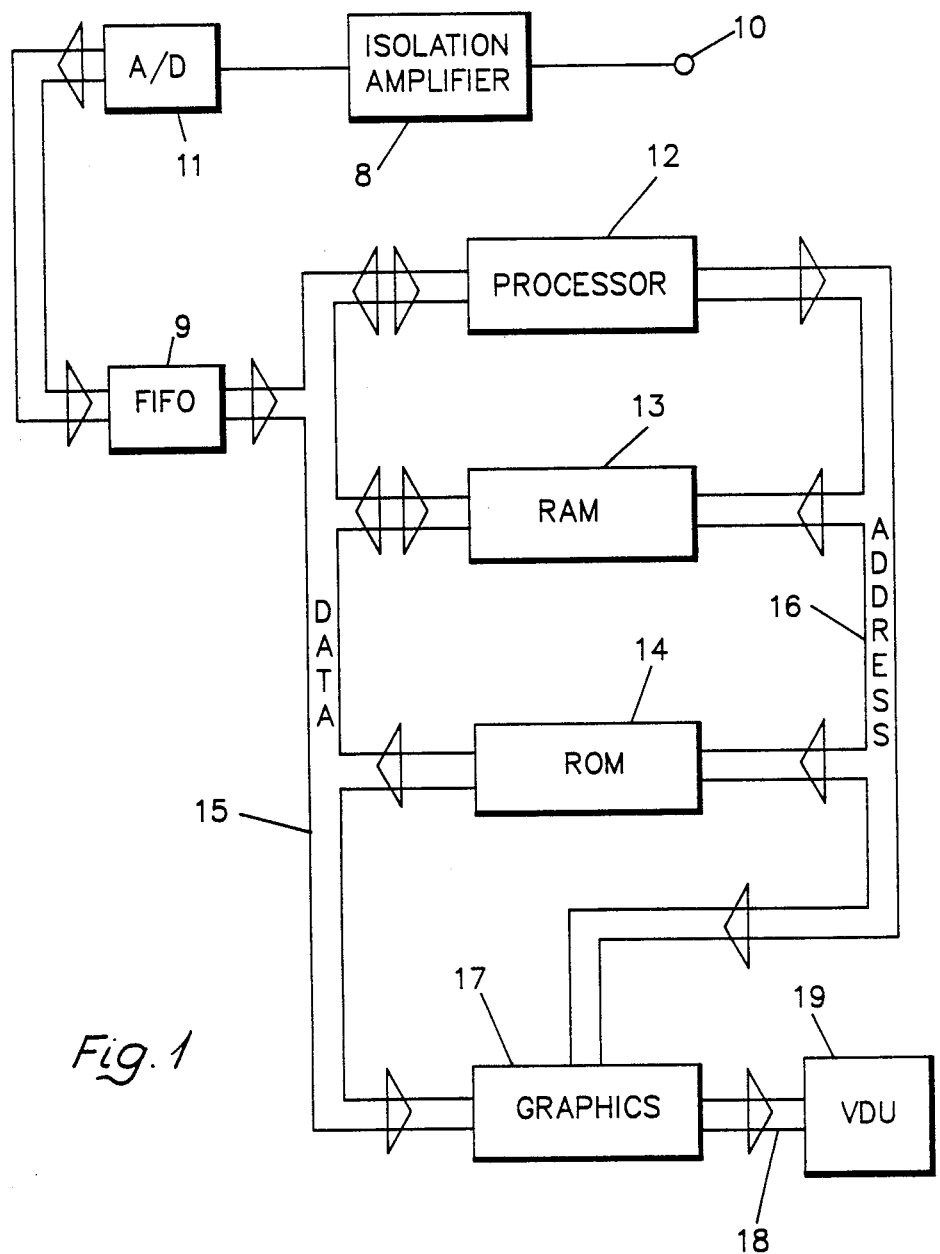
FIG. 1 is a block diagram of an apparatus according to the invention.

In FIG. 1 a scalp electrode 10 is connected by way of an isolation amplifier 8 (having a bandwidth between 3 dB points from 0.78 Hz to 250 Hz) to an analog-to-digital converter 11 and then to a first-in-first-out memory (FIFO) 9 and a processor system. Only the principal components of the processor system are shown: a processor 12, a random access memory (RAM) 13 and a read only memory (ROM) 14 connected by a data bus 15 and an address bus 16. The processor system also includes an integrated graphic circuit 17 connected to a visual display unit (VDU) 19 by way of wiring 18. Although a single processor is shown and an NEC type NS 32-16 processor can be used it may in some circumstances be convenient to use several processors. Equally the integrated graphics circuit 17 may be replaced by several interconnected integrated circuits.

If required the isolation amplifier 8 may also carry inter-uterine pressure signals from a transducer to a further analog-to-digital converter (not shown), having an output coupled to the bus 15.

Figure 2:
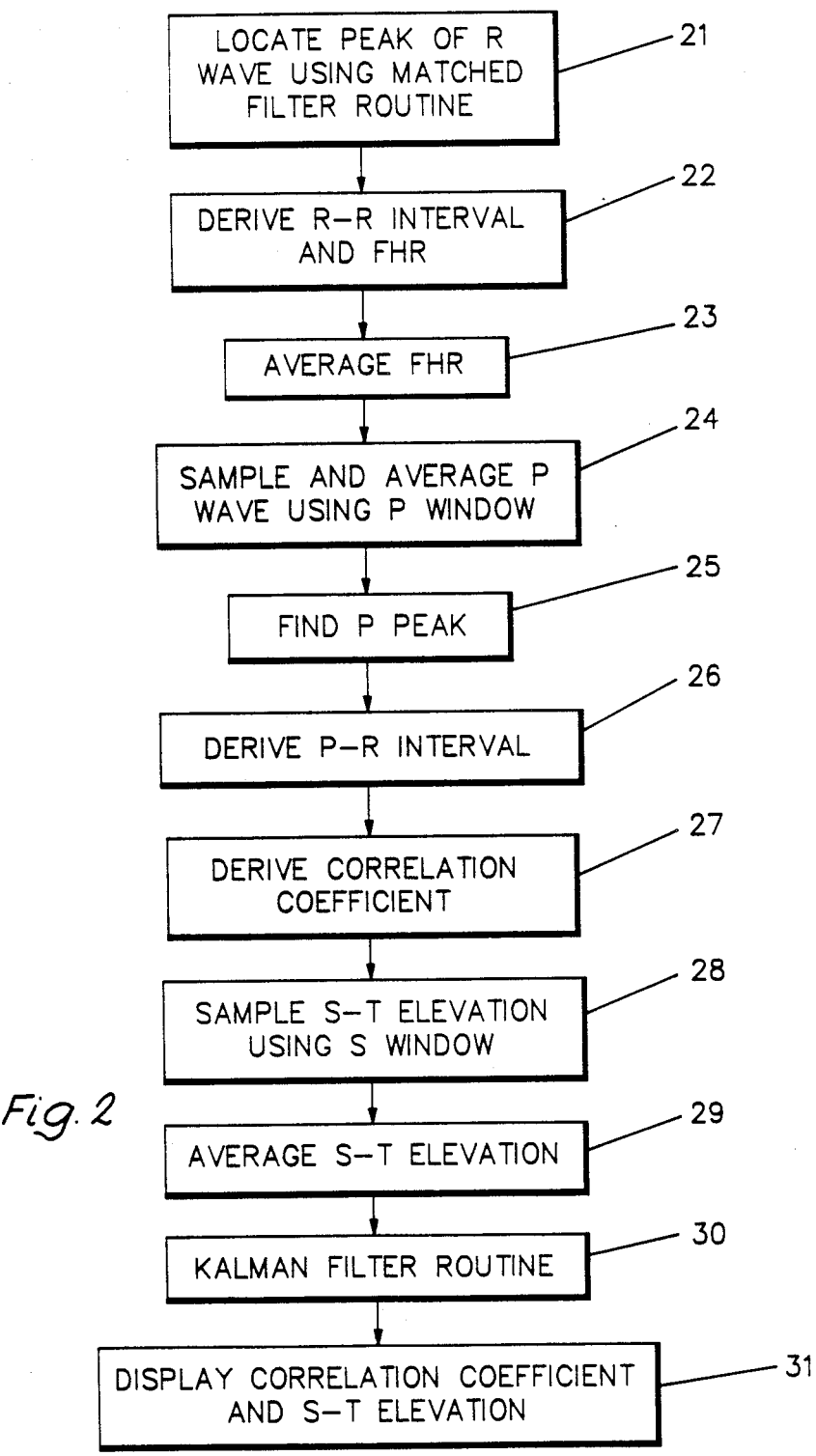
FIG. 2 is a flow chart of an algorithm carried out repeatedly by the processor of FIG. 1 to determine the conduction index and S-T elevation.
Figure 5A:
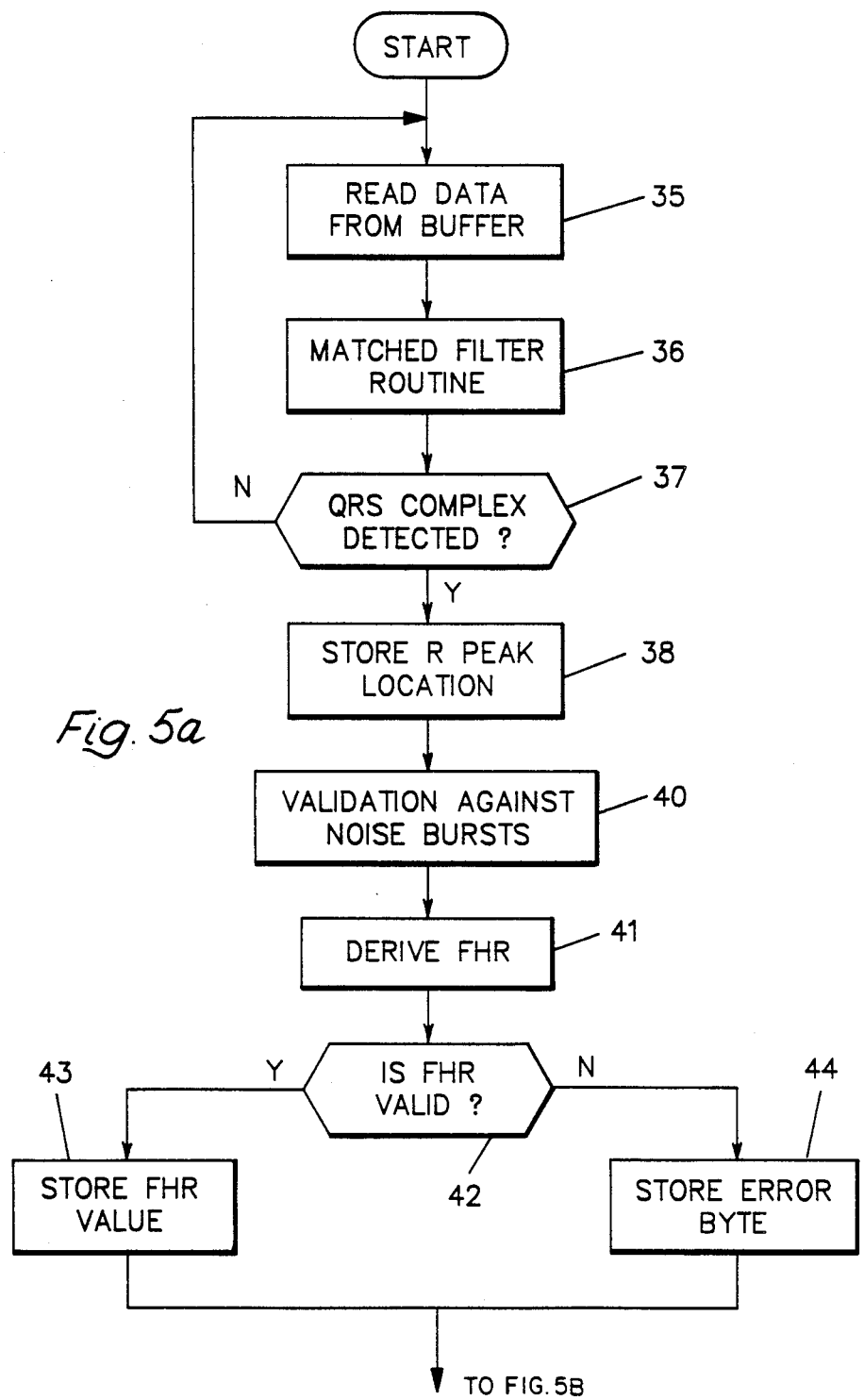
Figure 5B:
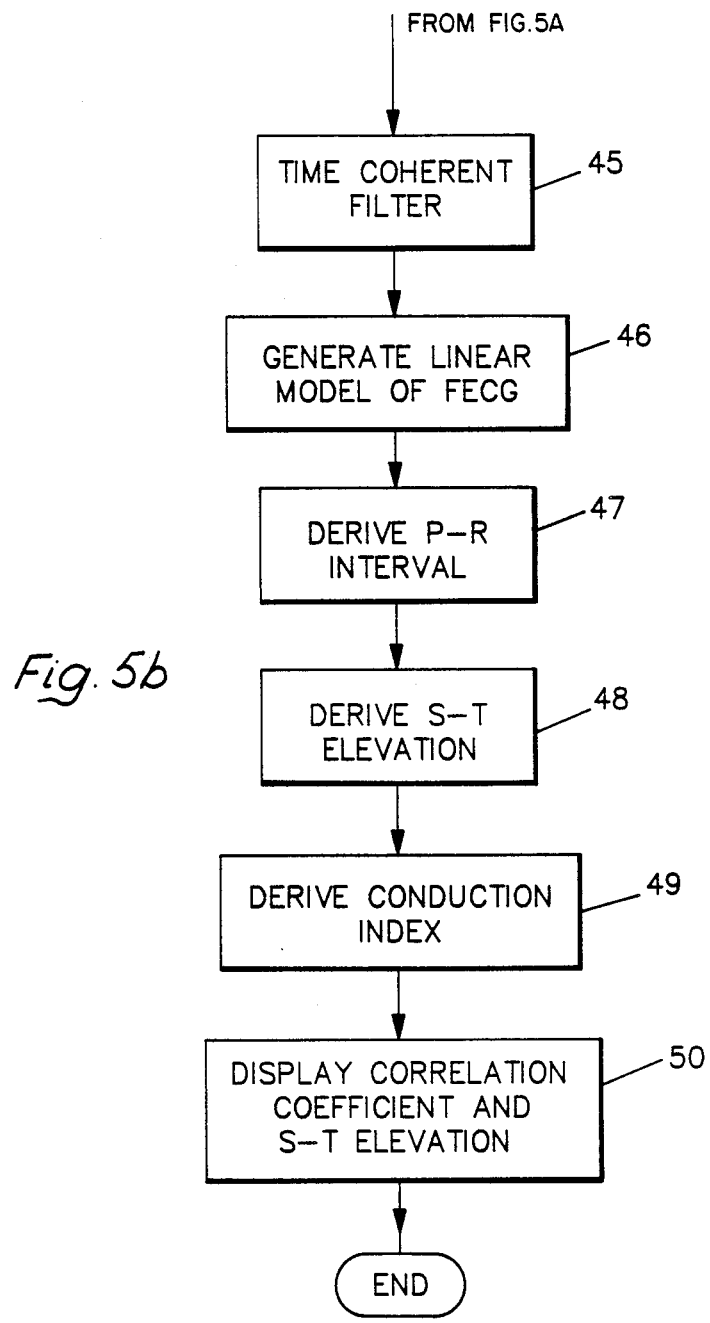

The ROM 14 contains a program which carries out the algorithm of FIG. 2, or that of FIGS. 5a and 5b.

As is well known a filter can be designed which rings, that is provides a high amplitude bi-directional pulse for a short interval when a particular waveform is applied to the filter. Such a filter, which can be in digital or analog form, is said to be matched to the waveform and is known as a matched filter. In operation, samples of the FECG of a fetus during labor are applied by way of the scalp electrode 10 and the analog-to-digital converter 11 to the processor 12. Use of the FIFO 9 is optional with the algorithm of FIG. 2. In an operation 21 of FIG. 2 the processor runs a digital matched filter subroutine matched to an averaged or standardised FECG derived from many fetuses. As a result the output of the matched filter subroutine contains peak values corresponding to ringing and these peak values correspond to the R peak of FIG. 3 which is an example of an FECG waveform enhanced to reduce noise.

In an operation 22, the processor 12 derives the interval between the R peaks of succeeding FECG waveforms and in the same operation the value derived is converted to the FHR calculated for one minute. To obtain an average value of FHR, each time the FHR is determined it is added to the previous value until an interval of one minute has elapsed when the total value is read out and the sum reset to zero (operating 23).

All FECG samples from the analog-to-digital converter 11 are stored in a portion of the RAM 13 but when an R peak is detected by ringing, the samples corresponding to the FECG waveform from the beginning of the P wave (about 150 msec before the R peak) to the end of the T wave (about 125 msec after the R peak) are transferred to a buffer portion of the RAM 13, each location in the buffer corresponding to a separate sample and therefore to a separate time in the incoming waveform.

That portion of the buffer containing samples corresponding to the P wave can be regarded as a window for averaging the P wave. Each FECG occurring in each one minute interval is transferred to the buffer with the R peaks at the corresponding locations as previous FECGs. The contents of corresponding buffer locations in the window for successive FECGs are added to provide a P wave averaged over one minute (operation 24). A double differential algorithm detects the peak of the averaged P wave (operation 25) and since the location in the buffer which stores the peak of the P wave is now known as is the location containing the R peak, the P-R interval is found simply by subtracting the address of one location from the other in an operation 26.

Averaging the P-R interval and fetal heart rate over one minute as in operations 23 and 24 reduces noise.

In an operation 27, the conduction index is obtained by deriving the Pearson correlation coefficient using ten previous values of the average P-R interval and the average FHR, each for one minute as derived in the operations 23 to 26. The expression for the Pearson coefficient is as follows:

$$r = \frac{N \sum_{L=1}^{N} PR \cdot FHR - \left(\sum_{L=1}^{N} PR\right) \cdot \left(\sum_{L=1}^{N} FHR\right)}{\sqrt{\left(N \sum_{L=1}^{N} PR^2 - \sum_{L=1}^{N} PR^2\right) \cdot \left(\sum_{L=1}^{N} FHR^2 - \sum_{L=1}^{N} FHR^2\right)}}$$

where N is the number of FHR ad P-R averaged intervals forming a data set within the 10 minute interval.

A further series of the buffer locations corresponding to the S-T segment form a window for this segment. Each time an FECG is read into the buffer the contents of these window locations are summed over an interval of one minute (operation 28) and expressed as a percentage of the maximum excursion of the Q-R-S complex (operation 29). The averaging process reduces noise but in order to reduce spurious signals still further the average S-T elevation may be subjected to a Kalman filtering subroutine in an operation 30 (see for example "Use of Optimal Estimation Theory, In particular the Kalman filter, in Data Analysis and Signal Processing", by William S. Cooper, Review of Scientific Instruments, 1986, Volume 57, No. 11, pages 2862–2869; and "An Overview of the Kalman Algorithm" by K. C. Shet and B. V. Rao, Int. Journal of Electronics, 1985, Volume 59, No. 6, pages 657–665).

Having determined the correlation index and the S-T elevation, a display of these quantities is generated in an operation 31 by passing appropriate values to the integrated graphic circuit 17 which controls the VDU 19. The display (see FIG. 4) shows a histogram of the conducting index and the one minute values of the S-T elevation. In the example shown the conduction index is generally negative for the first five hours and ten minutes of labor but then becomes positive indicating the possibility of acidosis. After a further hour the S-T elevation falls abruptly confirming acidosis in this birth (as was verified later).

In the method of FIG. 2, the FHR and the P-R interval are each averaged over one minute, but it is believed to be better to detect changes in these parameters from one fetal heart beat to the next. Thus an alternative and preferred method of carrying out the invention is now described in connection with FIGS. 5a and 5b.

Outputs from the A/D 11 of FIG. 1 are stored in the FIFO 9 and an interrupt is generated for the processor 12 every 32 ms. When the processor receives the interrupt, the current instruction is completed before branching to an interrupt service routine in which the processor is immediately disabled from further interrupt. Then 16 samples of raw FECG signal, stored in the first-in-first-out memory, are loaded into an input buffer (generated by software and forming part of the RAM 13) capable of holding four FECG waveforms. An input pointer for the buffer is increased by 16 and thus the pointer points to the position of the next entry to the buffer. However when the pointer reaches the end of the buffer it is reset to the beginning. Having transferred data to the buffer the processor 12 reverts to the main routine which has the flow chart of FIG. 5.

The FECG waveform is often buried in background noise and the QRS complex is the only recognizable component. Its detection implies the existence of an FECG waveform in the raw signal. A number of methods can be used for recognizing the QRS complex including a simple level detection method and a template matching method. However the preferred method is the use of a matched filter as mentioned above. Spectral analysis of fetal QRS complexes shows that the frequency content is mainly confined to the frequency band 17 to 30 Hz. A matched filter is designed to have a pass band exactly matching a spectrum of the QRS complex and can be realized either by hardware circuitry or software programming. Clearly in the present embodiment the matched filter is by software programming the processor 12. The digital matched filter used comprises a 50 Hz rejection (notch) filter, two 2-pole Butterworth low pass digital recursive filters and two 2-pole Butterworth high pass recursive filters. The 50 Hz rejection filter eliminates interference generated by the main supply, the 2-pole low pass recursive filters are cascaded together to form a fourth-order filter which rejects high frequency noise above 30 Hz and the two Butterworth high pass filters are cascaded together to limit d.c. drift and reject low frequency noise below 17 Hz. The filter coefficients required for the Butterworth filters can be calculated by implementing the software routine given by M. H. Akroyd in "Digital Filter: Computers in Medicine Series" (Ed. D. W. Hill), Butterworths, 1973. Thus in operation 35 of FIG. 5a data is read from the input buffer and used in a matched filter routine 36. If the spectrum of the raw data matches the pass band of the filter routine then the output samples describe a "ringing" output, that is a comparatively high amplitude oscillation which decays after a few cycles. A test 37 for a QRS complex is carried out by testing for digital outputs from the filter routine above a threshold level which indicates "ringing".

When the threshold is exceeded the most recent sample to be used in the matched filter is taken as the R peak of FIG. 3 and its position in the input buffer is stored as one of a number of R peak pointers (Operation 38). An FECG waveform or complex is then identified as 100 samples which precede the R peak and 150 samples which follow the peak in the input buffer.

To allow for variations in the signal level of signal reaching the A/D 11, the threshold level for detection of the QRS complex is preferably made variable. For example after setting the initial level at the beginning of monitoring to a convenient value, the threshold level can be varied in accordance with maximum levels in each newly detected QRS complex by subtracting a fixed amount from each new maximum level, the fixed amount being set to a value which is greater than the maximum variation between maximum outputs of two successive QRS complexes. When a sudden drop of signal strength occurs, caused for example by poor contact between an electrode and the fetal scalp, the threshold may no longer be exceeded. To overcome this problem the threshold level may be decremented when the threshold is not exceeded by a fixed amount until QRS complex detection resumes. However in order to guard against the detection of noise, a minimum threshold level may be provided. Additionally it is preferable that if noise spikes are detected then no adjustment of the threshold level occurs.

In detecting a QRS complex the threshold can be exceeded when a noise burst which has a similar frequency spectrum to a genuine QRS complex occurs. Such noise bursts can occur when the scalp clip of an electrode is disturbed during contractions or examinations of the fetus. A routine 40 discriminates against noise bursts by carrying out three tests on the 250 samples mentioned above and located partly before and partly after an R peak. In the first test the baseline of the FECG waveform is checked for slope. The samples representing the waveform are divided into three groups representing the P section, the QRS section and the T section (see FIG. 3). If the difference between the baselines of any pair of sections is larger than half the R to Q height or the R to S height, whichever is the larger, then the FECG waveform is classified as a noisy waveform. In the second test the background noise is checked. In a normal signal the amplitude of the background noise ripples is very small compared with the QRS height but sometimes a large amount of noise is picked up by the electrodes. To calculate noise strength the baselines of the P wave section and the T wave section from the first test are subtracted from each point within the corresponding section. The difference is then summed point by point over the section. If this average is more than a quarter of the QRS height the waveform is again classified as noisy. The third test is useful when the A/D 11 has been saturated possibly by disturbance of the scalp electrode. A counter in the processor 12 is set to count the number of sample points which have full scale deflection, either maximum or minimum, and if one third of the samples is full scale then the waveform is classified as noisy. When a waveform is classified as noisy a status flag is set and used later for validating FHR derivation and in enhancing the FECG.

In operation 38 the position of the R wave peak in the buffer is located. As mentioned above the input buffer holds four complete FECG waveforms so the interval between two R wave peaks can be calculated from the location of the current peak and the previous peak. The FHR value is then derived from:

$$\text{fetal heart rate} = \frac{30,000}{R\text{-}R \text{ interval}} \text{ beats per minute.}$$

A two part test 42 is then carried out to determine whether the FHR value is genuine since it may have been caused by invalid detection or noise spikes. The two part test comprises a first test in which the FHR value is checked against maximum and minimum allowed values set to 240 and 40 beats per minute respectively. If the first test is satisfied a second test is carried out in which the variation between the current value and the most recent of the three last valid FHR values is examined, the FHR value being rejected if it is more than a predetermined amount different from one of the previous values, the predetermined amount increasing with age of previous value, If the second test is not satisfied, reference is made to the result of the routine 40 and if this routine indicated a waveform which was not noisy a reference FHR value is used as the present value, provided the reference value has not been kept for more than a predetermined number of cycles of FHR calculation. The reference value is that of the most recently validated FHR value (provided it was not detected more than three cycles previously) and the predetermined number of cycles depends on how recently this value was validated: values validated in the last, penultimate, and antepenultimate cycle may be used for three, two and one cycles, respectively.

Depending on the result of the test 42 either the FHR value or a reference value is stored in an FHR buffer or an error byte is stored instead (operations 43 and 44). Since R peaks determined in the operation 38 may not be genuine and may instead belong to noise spikes, a pointer for the input buffer is used to indicate the locations of valid R peaks and is set when an FHR value is entered in the FHR buffer. It is not, of course, set when an error byte is entered in place of an FHR value.

When monitoring begins or after failure to maintain consistent FHR values, it is necessary to establish a genuine FHR value. Three successive calculated FHR values are required for this purpose, the variations between any pair of the values being checked against pre-set ranges. If this test is passed the most recent of the three values is then taken as a genuine reading which can be used as a reference in the second validation test above. Otherwise a further FHR reading is obtained until consistency in the FHR readings is achieved when a reference value is stored.

In raw FECG complexes the P and T waves are often poorly defined due to the presence of background noise. In the present embodiment a moving average technique is preformed on successive raw complexes of 250 samples located partly before and partly after an R peak in the input buffer (except those complexes classified as noisy by the routine 40) and provides an enhanced waveform for subsequent processing. In operation 45 each of the most recently located 250 data samples is summed with corresponding samples (in relation to the R peak) of a number of previous sets of 250 samples but the various sets are given weighting factors which decrease with the age of the sample set. Thus as time passes the contribution of each set to the sum becomes smaller. The enhanced waveform is taken as the sum of the weighted waveforms and stored in the RAM 13. Sudden changes in the FECG complex are smoothed out by an averaging effect and will not significantly distort the enhanced waveform. Only changes that last for at least a few fetal heart beats will appear in the enhanced FECG. It is known that the effect of this algorithm on the waveform is the same as passing each sample point of the raw complex through its own time coherent filter continuously, that is through 250 such filters. Time coherent filtering is the process of signal recovery from noise in the closest possible time relationship to the sample being recovered and other techniques may be used.

As mentioned in the paper "A simple software routine for the reproducible processing of the electrocardiogram" by C. J. Marvell and D. I. Kirk, published in the Journal of Biomedical Engineering, 1980, Volume 2, July, pages 216 to 220, there are advantages in generating a linear model of the FECG waveform, including providing an objective assessment of the waveform and good noise rejection. Thus an operation 46 generates a linear model from the stored samples of the enhanced waveform in the way described in the paper by Marvell and Kirk with the result shown in FIG. 6 where the model is made up of a number of intersecting linear segments designated 1' to 14'. The intersections of the lines are known as reference points and the time locations of the reference points are stored in a table in the RAM 13. However, they are first checked to see if they are within acceptable limits and if not an error byte is stored instead.

Figure 7:
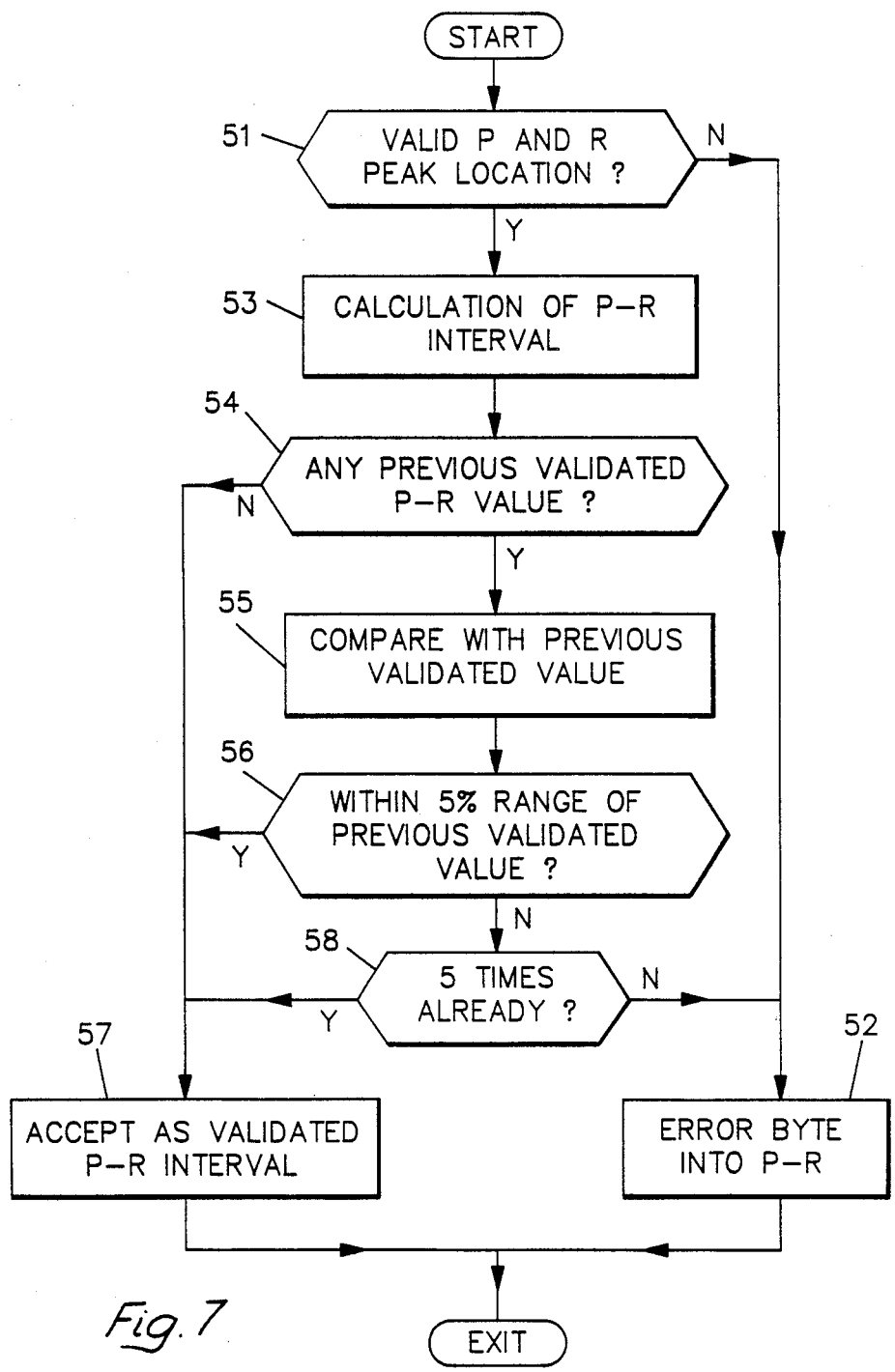
FIGS. 7 and 8 are flow charts of the routines of FIG. 5b for deriving the P-R interval and conduction index.

With this model various parameters can be derived including the P-R interval. The P-R interval is derived by a routine 47 shown in FIG. 7. A test 51 is carried out to determine whether the P and R time locations as stored in the operation 46 are valid or contain error bytes. If invalid an error byte is stored in a P-R buffer operation 52, but if valid the P-R interval is calculated by subtracting the time location of the reference point at the intersection of the lines 2' and 3' from that of the reference point at the intersection of the lines 7' and 8' in an operation 53. If, as indicated by a test 54, the P-R buffer contains a previous valid P-R value, the latest value is compared with the most recent stored value (operation 55) and if it is within 5% (operation 56) it is stored in the P-R buffer in an operation 57. If the test 56 is negative, a test 58 is carried out to check whether the test 56 has failed five times already. If to the P-R value is accepted as valid and the operation 57 takes place. If not an error byte is entered in the operation 52.

Figure 6:
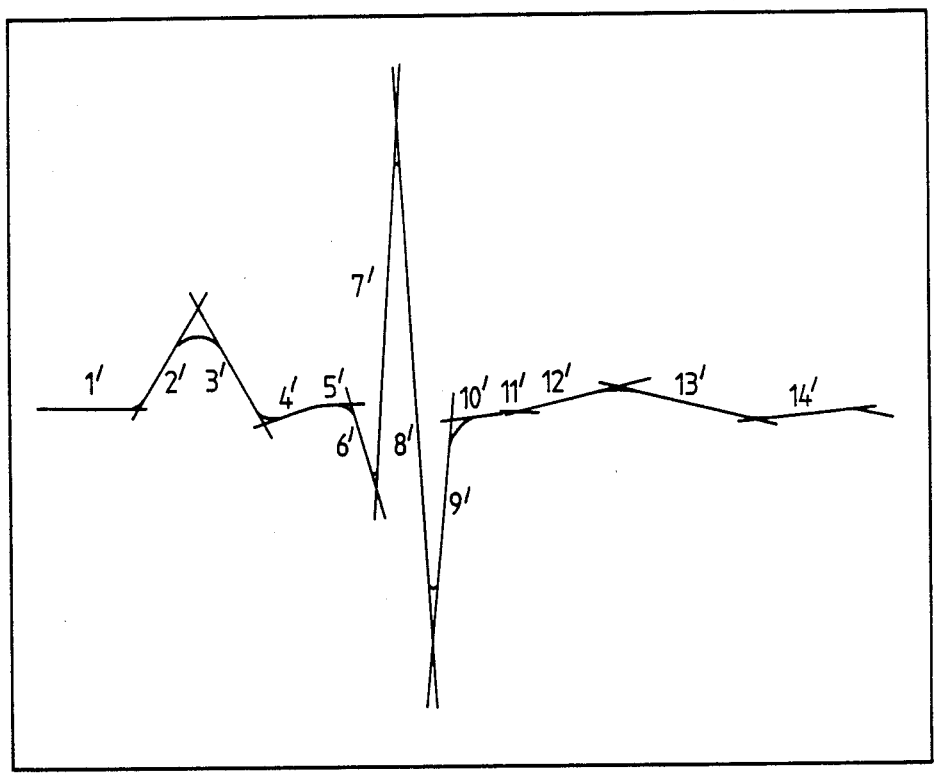
FIG. 6 shows a linear model of an FECG.

To derive the S-T elevation (operation 48), the height of the isoelectric line is first derived as the average of 10 data points of the enhanced FECG starting from 15 samples before the P wave onset (that is the intersection of lines 1' and 2' in FIG. 6). The S-T segment is a short segment after the termination of the S wave (the intersection of lines 9' and 10' in FIG. 6) and the onset of the T wave (the intersection of lines 11' and 12'), and the relative height of the R wave peak to the S wave peak, known as RS(p), or the R wave peak to the Q wave peak, known as RQ(p), is the elevation of the S-T segment which is calculated in an operation 47. Thus the S-T elevation is derived as a percentage from the following equation $$\% \ S\text{-}T \ \text{elevation} = \frac{100}{RS(p) \ \text{or} \ RQ(p)} \times (av - iso)$$

where "av" is average of the S-T segment amplitude and is defined as the average of 10 data points of the enhanced FECG starting at 5 data points after the S wave termination, and "iso" is the height of the isoelectric line calculated as described above. Percentage elevations greater than 100% mean the S-T segment is above the isoelectric line, while elevations less than 100% mean the S-T segment is depressed below the isoelectric line.

A routine 49 calculates the conduction index according to the previously given equation for "r" (expressed as a Pearson coefficient), except that the average values of FHR and P-R are replaced by the values found in the operation 41 and from the enhanced waveform and the linear model in the operation 47. The coefficient "r" is calculated every second using values of FHR and P-R stored over the most recent five minute interval. Thus there is a total of 300 points in each calculation (N=300), except as follows: where FHR or P-R values for a point are invalid as indicated by error bytes, that point is discarded and the total number of points is decremented. When the total falls below 200, the calculation is not completed and an error byte is produced as an indication.

Figure 8:
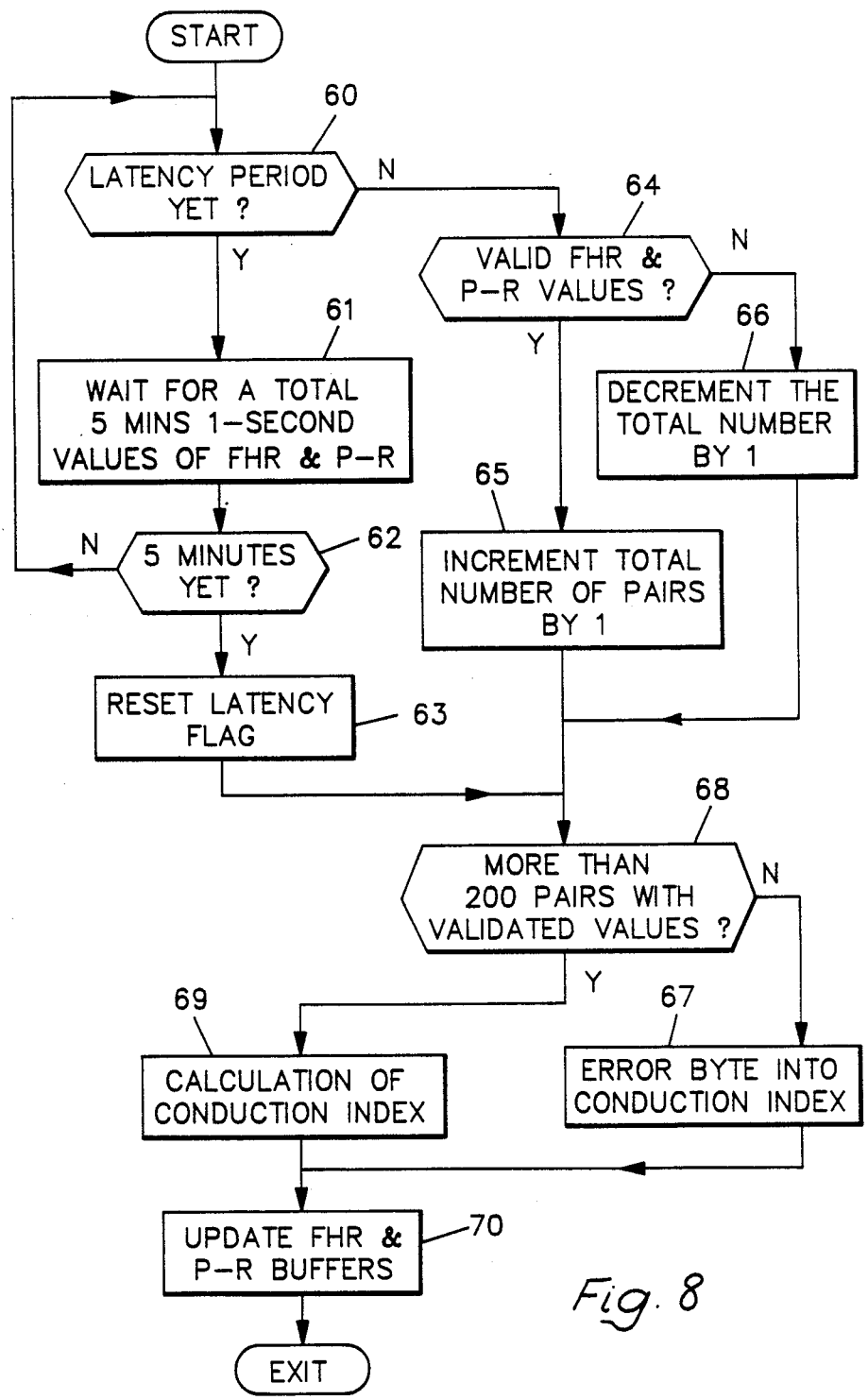

The routine 49 is shown in more detail in FIG. 8. Since the conduction index does not immediately become valid one measurements and calculations start, a latency period is allowed before the conduction index is calculated and displayed. A test 60 checks a status flag for the continuation of this period and if it is satisfied, a waiting period 61 of five minutes occurs and then a test 62 is followed by resetting the status flag (operation 63) if the period is over. If the flag is reset at the test 60, a test 64 is made for valid FHR values (in the FHR buffer) and R-R values, and a count of pairs of such values is incremented by one operation 65), if valid. Otherwise the count is decremented (operation 66) and an error byte entered into a conduction index buffer (operation 67). Following the operations 63 or 65, the number of FHR and R-R pairs are checked (test 68) and if greater than 200, the conduction index is calculated as mentioned above (operation 68) and then the FHR and R-R buffer are updated in an operation 70.

Having derived the correlation coefficient and the S-T elevation, these quantities are displayed on an oscilloscope or by means of a printer, or both, in an operation 50 which is equivalent to the operation 31 of FIG. 2.

While the invention has been specifically described it will be realized that it can be put into practice in other ways. For example other types of correlation coefficients and values averaged over other time intervals may be used. The processes and apparatus for monitoring fetal health in the general way described may also be varied.

We claim:

1. An apparatus for monitoring fetal health during labor comprising:
   means for continually sampling the electrocardiogram of a fetus and for continually outputting sampled signals; and
   processing means for receiving said output sampled signals and in response thereto deriving signals representative of the P-R interval of the fetal heart, for repeatedly deriving a signal representative of the fetal heart rate, and for obtaining an indication relationship between directions of change, of the P-R interval and in the fetal heart rate or a repetition period of the fetal heart, for providing an indication of fetal health whereby an indication is given of shortening or lengthening of the P-R interval as the fetal heart rate increases or decreases.

2. An apparatus according to claim 1 wherein the said processing means repeatedly obtains a signal representative of elevation of the S-T interval of the fetal electrocardiogram.

3. An apparatus according to claim 2 wherein said processing means determines the elevation of the S-T interval above an isoelectric line, and calculates an isoelectric line from digital samples, representing a fetal electrocardiogram, over an interval between the end of the T wave of a fetal electrocardiogram cycle preceding a current such cycle, as represented by the said samples, and the beginning of the P wave of the current cycle, as also represented by the said samples.

4. An apparatus according to claim 2 wherein said processing means carrying out a process of, or equivalent to, time coherent filtering of fetal electrocardiogram values to provide an enhanced representation of the fetal electrocardiogram, the enhanced representation of the fetal electrocardiogram being used in deriving the signal representative of the elevation of the S-T interval and/or the indication of the said correlation.

5. An apparatus according to claim 4 wherein said processing means receiving a succession of sets of digital samples representing a fetal electrocardiogram and said process being continually carried out by weighting the values of a plurality of the most recent sets with weightings which decrease with the age of the set, and summing corresponding values of the sets relative to the R-wave peak to provide the enhanced representation.

6. An apparatus according to claim 1 wherein said processing means repeatedly derives an indication of the correlation between the P-R interval and the fetal heart rate or the repetition period of the fetal heart, whereby a sign of the correlation gives an indication of said relationships.

7. An apparatus according to claim 6 wherein said processing means derives a Pearson correlation coefficient from values representing the P-R interval and values representing the fetal heart rate.

8. An apparatus according to claim 7 wherein said P-R values and fetal heart rate values are averaged by said processing means over predetermined intervals of duration in the range 40 to 80 seconds before being used as the values representing the P-R interval and fetal heart rate values to derive the Pearson coefficient.

9. An apparatus according to claim 8 wherein a predetermined number of each of the said average values in a range 8 to 12 is used in deriving the Pearson correlation coefficient.

10. An apparatus according to claim 6 including means for displaying an indication of the correlation as a histogram.

11. An apparatus according to claim 6 said processing means repeatedly obtaining a signal representative of the magnitude of S-T interval of the fetal electrocardiogram and further includes means for displaying the magnitude of the S-T interval.

12. An apparatus according to claim 1 wherein said processing means employing a matched filter algorithm to determine when the R peak of each fetal heart cycle occurs, and to derive the fetal heart rate from successive detected R peaks.

13. An apparatus according to claim 12 wherein said processing means employing a periodically occurring temporal window positioned relative to the R peak to sample the P wave of an FECG, and to determine the P peak from the samples obtained.

14. An apparatus according to claim 12 said processing means being arranged, in operation, to employ a periodically occurring temporal window positioned relative to the R peak to sample the T wave of an FECG, and to determine the magnitude of the S-T segment from the sample obtained.

15. A method of monitoring fetal health during labor comprising repeatedly obtaining a signal representative of the P-R interval of the fetal heart, repeatedly obtaining a signal representative of the fetal heart rate, and providing an indication of relationship between directions of change, of the P-R interval and in the fetal heart rate or a repetition period of the fetal heart to provide an indication of fetal health whereby an indication is given of shortening or lengthening of the P-R interval as the fetal heart rate increases or decreases.

16. A method according to claim 15 including repeatedly obtaining a signal representative of an elevation of S-T interval of the fetal electrocardiogram.

17. A method according to claim 16 wherein the elevation of the S-T interval above an isoelectric line is determined, the isoelectric line being calculated from digital samples, representing a fetal electrocardiogram, over an interval between the end of the T wave of a fetal electrocardiogram cycle preceding a current such cycle, as represented by the said samples, and the beginning of the P wave of the current cycle, as also represented by the said samples.

18. A method according to claim 16 including displaying the said elevation of the S-T interval.

19. A method according to claim 15 including repeatedly obtaining an indication of the correlation between the P-R interval and the fetal heart rate or the repetition period of the fetal heart, whereby a sign of the correlation gives an indication of said relationships.

20. A method according to claim 19 wherein a Pearson correlation coefficient is derived from values representing the P-R interval and values representing the fetal heart rate.

21. A method according to claim 19 further comprising carrying out a process of time coherent filtering of fetal electrocardiogram values to provide an enhanced representation being used in deriving the said correlation.

22. A method according to claim 21 wherein a succession of sets of digital samples is received representing a fetal electrocardiogram and the said process is continually carried out by weighting the values of a plurality of most recent sets with weightings which decrease with the age of the set, and summing corresponding values of the sets relative to the R-wave peak to provide the enhanced representation.

23. A method according to claim 19 including displaying an indication of the correlation as a histogram.

24. A method according to claim 15 wherein a matched filter algorithm is employed to determine when the R peak of each fetal heart cycle occurs, and to derive the fetal heart rate from successive detected R peaks.

* * * * *